United States Patent [19]
Barath et al.

[11] Patent Number: 5,112,305
[45] Date of Patent: May 12, 1992

[54] CATHETER DEVICE FOR INTRAMURAL DELIVERY OF THERAPEUTIC AGENTS

[75] Inventors: Peter Barath, West Hollywood, Calif.; Ferenc Denes, Budapest, Hungary

[73] Assignee: Cedars-Sinai Medical Center, Los Angeles, Calif.

[21] Appl. No.: 598,405

[22] Filed: Oct. 16, 1990

Related U.S. Application Data

[63] Continuation-in-part of Ser. No. 472,898, Jan. 31, 1990.

[30] Foreign Application Priority Data

Jun. 20, 1989 [HU] Hungary ............................. 3145/89

[51] Int. Cl.⁵ ............................................. A61M 29/00
[52] U.S. Cl. ........................................ 604/96; 604/101
[58] Field of Search .................. 604/96, 99, 101, 265, 604/266, 51–53, 104, 97

[56] References Cited

U.S. PATENT DOCUMENTS

| 3,971,385 | 7/1976 | Corbett | 604/96 |
| 3,981,299 | 9/1976 | Murray | 604/43 |
| 4,417,576 | 11/1983 | Baran | 604/96 |
| 4,641,653 | 2/1987 | Rockey | 604/96 |
| 4,693,243 | 9/1987 | Buras | 604/96 |
| 4,994,072 | 2/1991 | Bhate et al. | 604/96 |
| 5,002,531 | 3/1991 | Bonzel | 604/96 |
| 5,017,370 | 5/1991 | Hunter et al. | 604/53 |
| 5,021,044 | 6/1991 | Sharkawy | 604/53 |

Primary Examiner—C. Fred Rosenbaum
Assistant Examiner—Sharon Finkel
Attorney, Agent, or Firm—Lyon & Lyon

[57] ABSTRACT

The present invention discloses a method of treatment of an atherosclerotic blood vessel. Specifically, therapeutic agents are delivered by means of a specialized catheter system to the deeper layers of the vessel wall with only minimal interuption of the vessel endothelium. This system will allow high local concentrations of otherwise toxic agents directly at the site of an atherosclerotic plaque. This invention will hopefully reduce the incidence of late restenosis attributed to cellular hyperplasia or rethrombosis.

2 Claims, 5 Drawing Sheets

CATHETER DEVICE FOR INTRAMURAL DELIVERY OF THERAPEUTIC AGENTS

This application is a continuation-in-part of copending application Ser. No. 472,898 filed on Jan. 31, 1990

This invention relates generally to the medical and veterinary medical field of atherosclerotic lesion treatment. Specifically, a device is disclosed that allows the localized administration of various therapeutic agents into the wall of an involved vessel. One use of this device will be to prevent post angioplasty vascular restenosis precipitated by either reoccurrence of the initial thrombotic lesion or by hyperplasia of the local vessel cellular components.

BACKGROUND OF THE INVENTION

Atherosclortic Cardiovascular Disease (ASCVD) is the most common cause of death in industrial countries. (AJR 150: 1263-1269 (1988)). Peripheral Vascular Disease (PVD) also contributes to the morbidity and mortality rates in these populations. In both diseases, damage is mediated by an occlusive lesion of the involved vessel. This lesion is generically called a thrombus. A thrombus is an aggregate of elements formed on the wall of an involved vessel from constituents of the blood in response to a thrombogenic stimuli. This process of thrombus formation is termed thrombosis. Body tissues distal to the occlusion are deprived of their normal blood flow and its ensuing benefits.

Over the years various medical interventions have been employed to remove or otherwise treat an offending thrombotic lesion. Although the surgical procedure Coronary Artery By-Pass Grafting (CABG) remains the gold standard for treatment of lesions involving the coronary vessels of the heart, less invasive methods have an established role in this treatment.

Percutaneous transluminal angioplasty (PTA), or balloon angioplasty, has proven to be a useful procedure for the treatment of localized atherosclerotic lesions of both coronary and peripheral vessels. (Merck Manual, 15th Ed., pg 559). Simply stated, this technique involves the cannulation of an affected vessel with special catheters. An uninflated balloon portion of the catheter is introduced into the narrowed vessel lumen so that it is juxtapositioned to the lattice-like network of the forming thrombus. Inflation of the balloon portion of the catheter compresses the offending thrombus against the vessel wall thereby restoring lumen patentability.

Vessels of the human body are lined by a smooth surface known as the endothelium. The innermost layer of the endothelium is called the intima. This impervious layer improves vascular bloodflow hemodynamics and shields deeper vessel wall layers from contact with the blood itself. Unfortunately, successful PTA invariably involves some interruption of this lining with a resulting violation of the barrier it provides between the deeper placed smooth muscle cells (SMC) of the vessel wall and the blood itself. Local hemodynamic flow characteristics are also affected.

Although many questions are left unanswered, it is believed that some combination of these two factors leads to a late recurrence of partial vessel occlusion in 35-40% of otherwise successful PTA procedures. Indeed, about one-third of all patients treated with PTA return for a second or third procedure, thus reducing the long term benefits of the procedure. Therefore, a need continues to exist to increase the long term benefit of PTA by preventing or reducing vessel restenosis.

One mechanism of vessel restenosis is SMC hyperplasia. In histologic sequences that resemble tumor growth, the vessel SMCs dedifferentiate from a contractile to a synthetic phenotype, followed by intense proliferation and the production of connective tissue. It has been proposed that one method of combating restenosis might be the administration of various therapeutic agents known to block intimal and smooth muscle hyperplasia. Systemically administered drugs such as anticoagulants, vasodilator, etc. have so far proven ineffective to prevent restenosis. More radical treatment involving agents such as cytostatic drugs or general enzyme blockers may prevent smooth muscle cell proliferation but often these agents are toxic to humans at the levels necessary to effectively block development of the involved pathology. For that reason, the current inventor has proposed local administration of such agents. In particular, cytotoxic antitumor agents are suggested as a means of selectively damaging the hyperplastic SMCs.

Problems remain however in the exact method by which this local administration should be accomplished. Conventional methods of drug therapy, as discussed above, often result in blood levels of the cytotoxic agent that are dangerous for the patient. Another problem of systemic administration is the inevitable fluctuations of serum drug concentrations that it produces. Even with local administration of these agents, one must consider that the normal bloodflow of the vessel will dilute the local concentration of the therapeutic agent by a washout effect. The need remains, therefore, to devise a system whereby otherwise toxic therapeutic agents are concentrated and localized within the affected vessel wall segment.

SUMMARY OF THE INVENTION

The present invention relates to a novel catheter system and method that will deliver chemical agents intramurally at the precise vessel segment that is diseased but without allowing the agents to diffuse distally into the bloodstream. One embodiment of the present invention employs a double lumen catheter that has additional tubular extensions projecting at various angles from the outer surface of the outermost lumen. By abruptly increasing the pressure in the outer lumen, the tubular extensions deliver the therapeutic agent to locations deep within the vessel wall. Another embodiment of the invention would allow blood flow to continue distally while absorption occurred more slowly within particular alternating arcs of the vessel lumen. In any embodiment, the therapeutic agents could be bound to macromolecules to enhance their ability to avoid washout from the vessel wall, if this were desired and feasible.

A more comprehensive understanding of one embodiment of the present invention will be evident after reviewing the forthcoming diagrammatic representations with their detailed description.

BRIEF DESCRIPTION OF THE DRAWINGS

From the balloon surface (1) tubular extensions (10) with lumen (11) stick out. The two ends of the balloon (12) are free of extensions and serve to isolate the area where fluid is burst into the vessel wall from the other parts of the vessel lumen.

Figure 1:
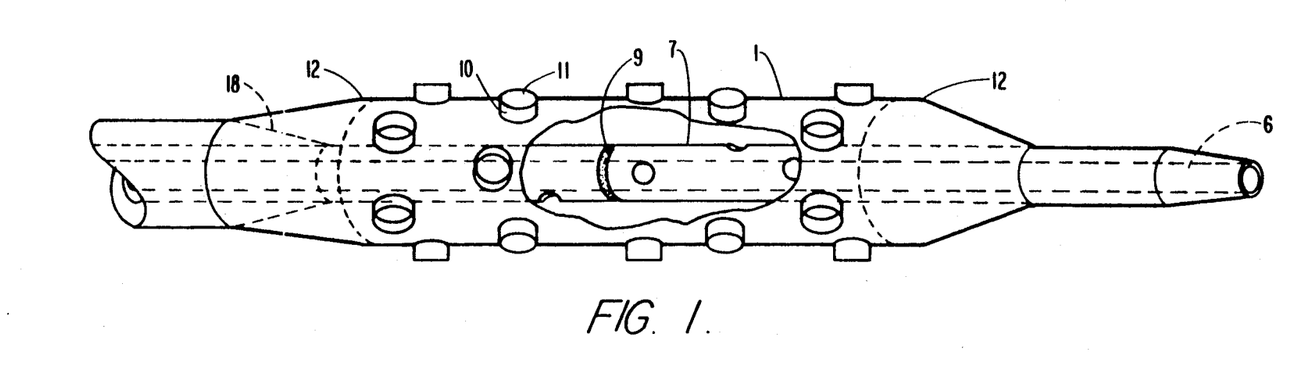
FIG. 1 is a longitudinal section of the inflated balloon (1), the catheter shaft (2) with its Luer connector (3), the central lumen (4) with its Luer connector (5). The catheter ends in a tapered luminal tip (6). The central lumen (4) is to accommodate a steerable guide wire or to inject contrast material. The catheter shaft (2) is tapered into the shaft of the balloon (7) which is perforated by several sideholes (8) and has a radiopaque platinum marker (9).
Figure 1A:
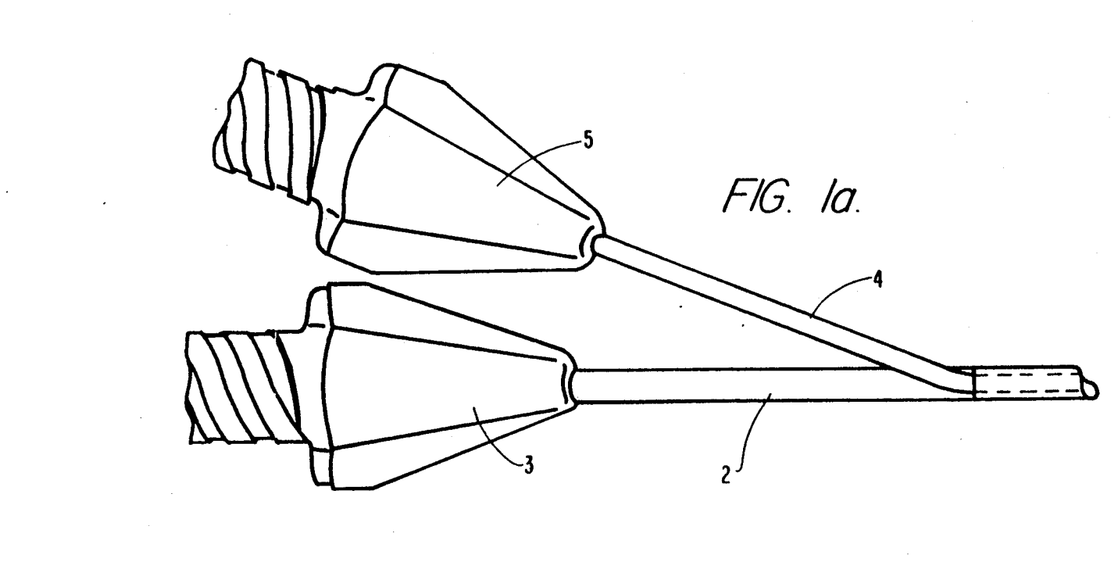
Figure 2:
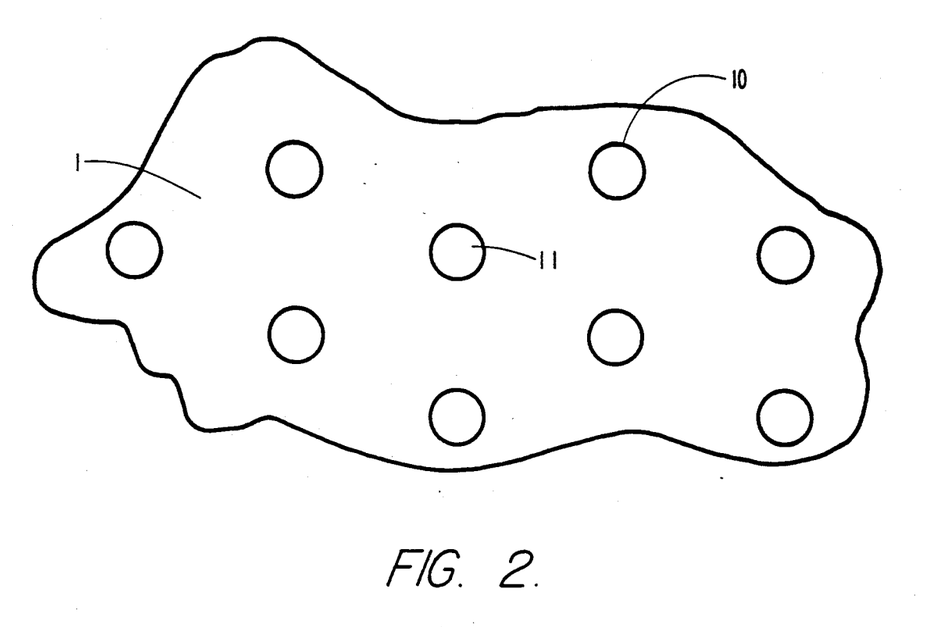
FIG. 2 shows a detail of the balloon surface (1) with the tubular extensions (10) and with their holes (11). While the size of the catheter and the balloon is determined by vessel size, the diameter (a) and the length (b) of the tubular extensions (10) are 0.50 and 0.25 mm, respectively.
Figure 3:
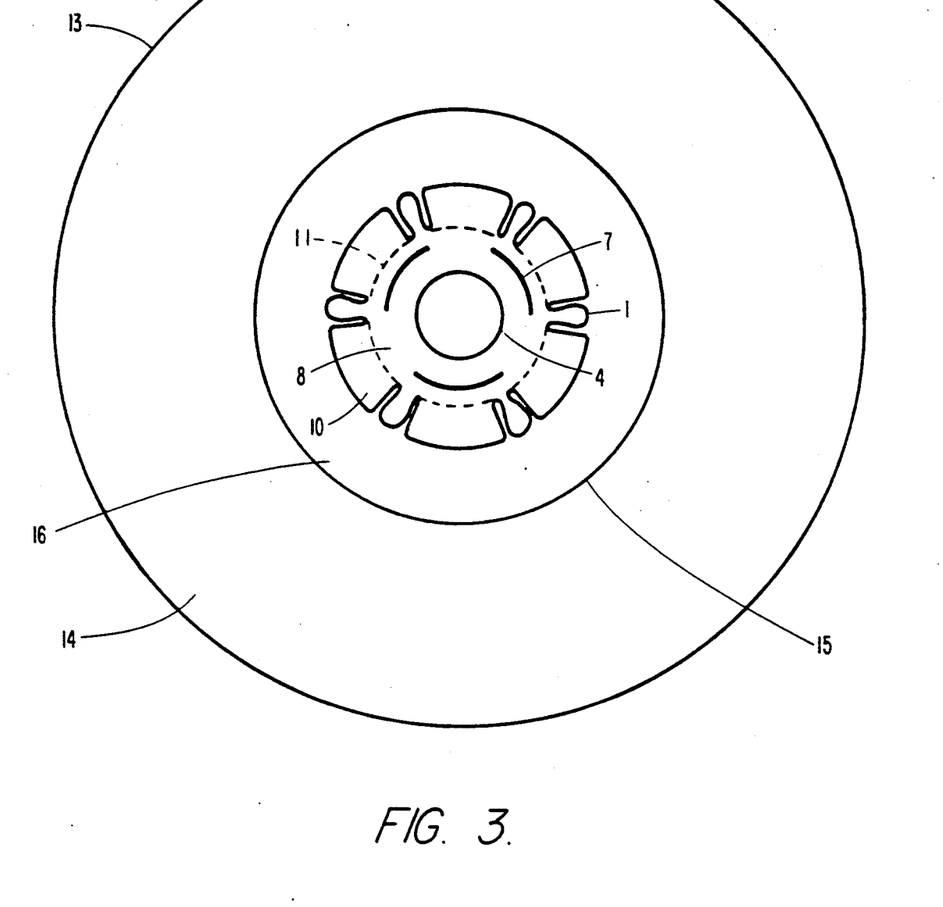
FIGS. 3 through 5 demonstrate the use of the delivery system.
Figure 4:
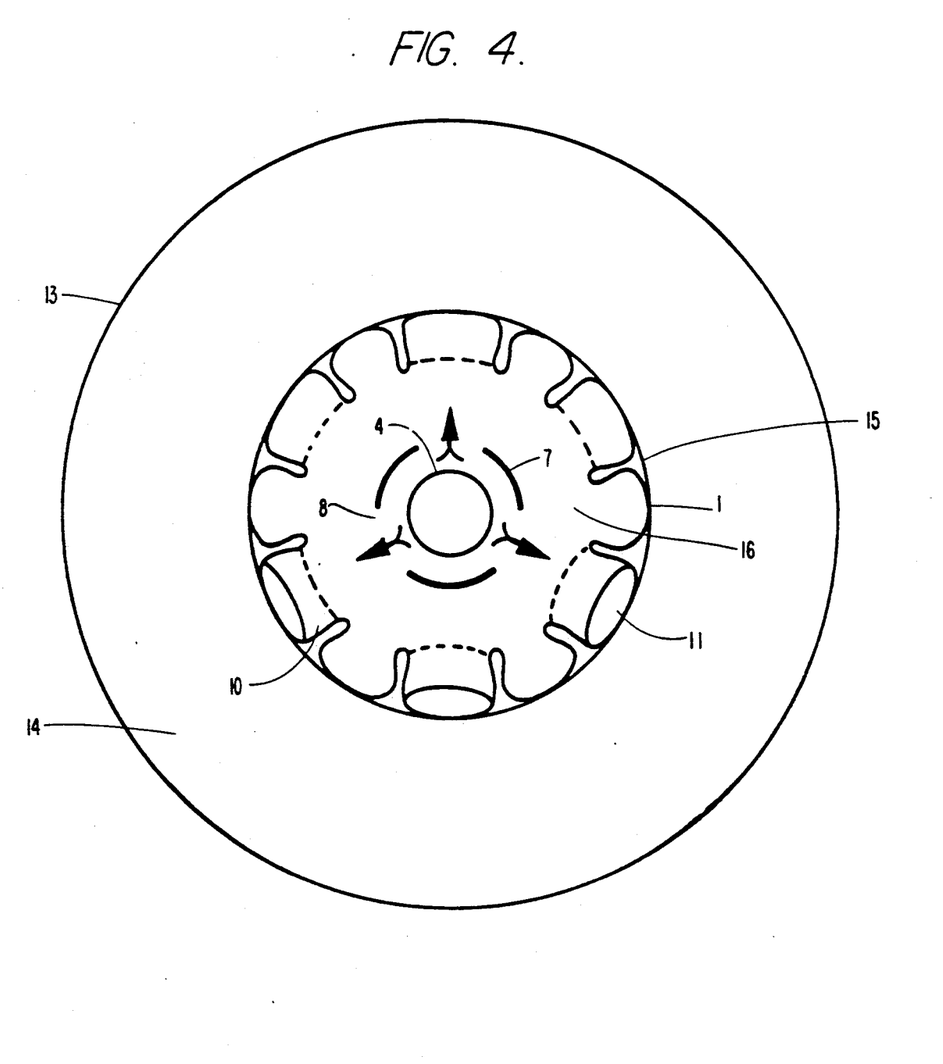

The catheter is inserted into the vessel segment which had undergone angioplasty, over a guide wire in a deflated state (FIG. 3). The drawing shows the adventitial (13), endothelial (15) surfaces of the vessel, the vessel wall (14) and the vessel lumen (18). The tubular extensions (10) of the balloon (11) are inverted when the balloon is deflated (insertion phase). After positioning the balloon within the desired vascular segment, the catheter is connected to an angiographic injector through the Luer connector of the catheter shaft (3 on FIG. 1). The pressure in the balloon is slowly built up by injection of a fluid form of the chemical agent at a low flow rate to the point when the balloon surface (1) closely leaned against the endothelial surface of the vessel (15). At this point the tubular extensions (10) are not penetrating into the vessel wall (FIG. 4, inflation phase), and fluid is hardly leaking through the lumens of the extensions (11).

As the flow rate and the pressure is abruptly increased in the balloon by injection of a small volume (0.25-0.50 ml) from the injector (FIG. 5, bursting phase) the tubular extensions (10) suddenly penetrate into the vessel wall (15) and the fluid (17) is propelled into the deeper layers of the wall (15) through the holes of the extensions (11).

Figure 5:
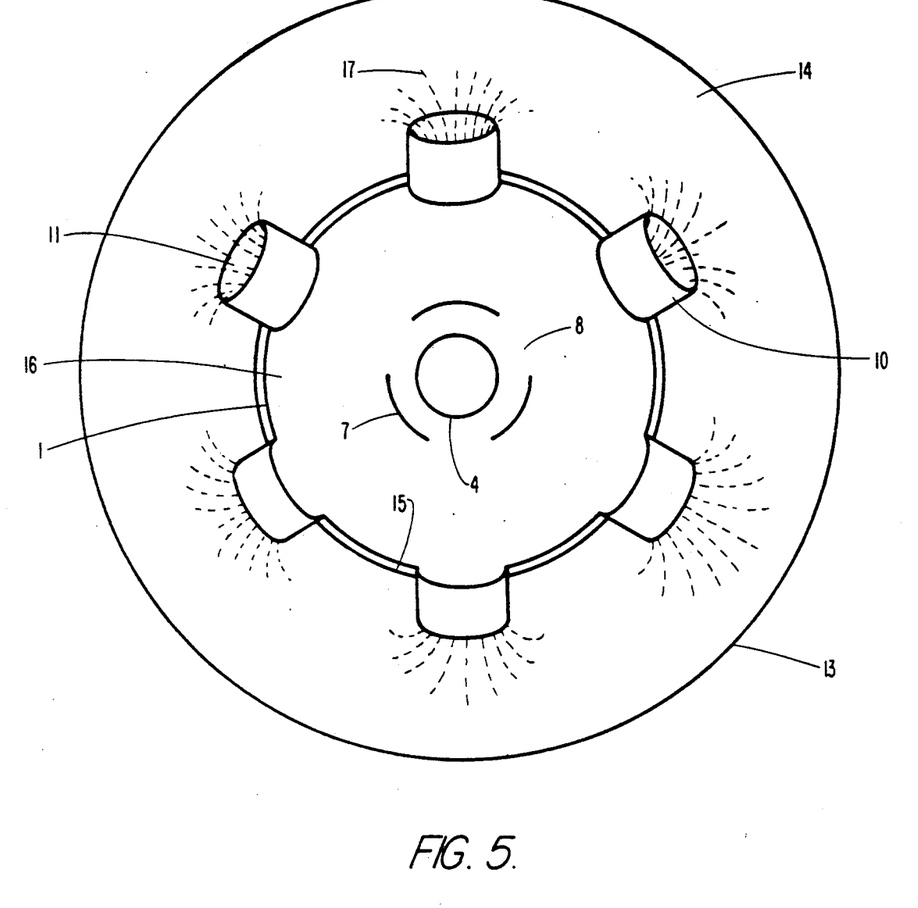

After 10 seconds, the balloon is deflated and removed from the vessel.

INDEX OF FIGURE LABELS

1. Balloon surface;
2. Catheter shaft;
3. Luer connector of the catheter shaft;
4. Central lumen;
5. Luer connector of the central lumen;
6. Tapered tip of the catheter;
7. Tapered shaft of the catheter;
8. Slide holes on the shaft;
9. Radiopaque platinum marker;
10. Tubular extension;
11. Lumen of the tubular extension;
12. Extension-free (occluding) area of the balloon;
13. Adventitia;
14. Vessel wall;
15. Endothelial surface of the vessel;
16. Fluid; and
17. Fluid burst into the vessel wall.

I claim:

1. A method of treating a blood vessel which contains an atherosclerotic lesion whereby a therapeutic agent is delivered into the vessel wall at or near the side f the atherosclerotic lesion comprising:

insertion of a catheter device system into a diseased blood vessel, the catheter being one which contains an inflatable balloon studded with hollow tubular extensions that communicate between the outer surface of the balloon and the inner lumen of the catheter device system;

slow filling of the catheter balloon so that the balloon surface's tubular extensions abut the inner vessel wall; and, rapid infusion of a bolus of a therapeutic agent fluid sufficient to effect bursting of the vessel's endothelium by the tubular extensions and delivery of a therapeutic agent to the deeper layers of the vessel wall through the extensions.

2. A catheter device and system useful in the treatment of blood vessels or other hollow viscera of the body, said catheter comprising:

a centrally hollow shaft having proximal and distal ends, said central portion comprising a first longitudinally extending lumen with an opening on its proximal end adapted to receive therapeutic fluid for a guide wire, and a second longitudinally extending lumen circumferentially disposed around and capable of communicating with the first longitudinally extending lumen and with a similarly adapted proximal end;

a plurality of inflatable balloon type regions longitudinally and circumferentially disposed along the axis of said second longitudinally extending lumen and capable of fluid communication therewith;

a plurality of radially extending hollow tubular studs disposed along said inflatable regions extending outwardly from said catheter device and capable of fluid communication directly to either or both of the inner lumens.

* * * * *

UNITED STATES PATENT AND TRADEMARK OFFICE
CERTIFICATE OF CORRECTION

PATENT NO. : 5,112,305

DATED : May 12, 1992

INVENTOR(S) : Peter Barath et al.

It is certified that error appears in the above-identified patent and that said Letters Patent is hereby corrected as shown below:

Column 4, claim 2, line 37, please delete the word "for" and replace it with the word --or--.

Signed and Sealed this

Thirty-first Day of August, 1993

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,112,305

DATED : May 12, 1992

INVENTOR(S) : Peter Barath et al.

It is certified that error appears in the above-identified patent and that said Letters Patent is hereby corrected as shown below:

Column 1, line 18, delete "Atherosclortic" and replace with --Atherosclerotic--.

Column 2, line 12, delete "vasolidator," and replace with --vasolidators--.

Column 2, line 19, delete "has" and replace with --have--.

Column 3, line 19, delete "," and replace with --and--.

Column 3, line 20, delete "and the vessel lumen (18)" and replace with --.--.

Signed and Sealed this

Twenty-sixth Day of October, 1993

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT : 5,112,305

DATED : May 12, 1992

INVENTOR(S) : Peter Barath

It is certified that error appears in the above-identified patent and that said Letters Patent is hereby corrected as shown below:

Column 1, line 18, delete "Atherosclortic" and replace with --Atherosclerotic--.

Column 2, line 12, delete "vasodilator," and replace with --vasodilators,--.

Column 2, lines 18-19, delete the word "inventor" and replace with the word --inventors --.

Column 2, line 19, delete "has" and replace with --have--.

Column 3, line 19, delete "," and replace with --and--.

Column 3, line 20, delete "and the vessel lumen (18)" and replace with --.--.

UNITED STATES PATENT AND TRADEMARK OFFICE
CERTIFICATE OF CORRECTION

PATENT NO. : 5,112,305

DATED : May 12, 1992

INVENTOR(S) : Peter Barath

It is certified that error appears in the above-indentified patent and that said Letters Patent is hereby corrected as shown below:

COLUMN 4, line 14, delete "side f" and replace it with the word ---side of---.

This certificate supersedes Certificate of Correction issued October 26, 1993.

Signed and Sealed this

Twenty-fifth Day of October, 1994

Attest:

BRUCE LEHMAN

Attesting Officer

Commissioner of Patents and Trademarks